United States Patent [19]

Seiwell

[11] 4,096,185

[45] Jun. 20, 1978

[54] PREPARATION OF P-AMINOBENZOTRIFLUORIDE

[75] Inventor: Linda P. Seiwell, Wilmington, Del.

[73] Assignee: E. I. Du Pont de Nemours and Company, Wilmington, Del.

[21] Appl. No.: 771,067

[22] Filed: Feb. 23, 1977

Related U.S. Application Data

[63] Continuation-in-part of Ser. No. 647,495, Jan. 8, 1976, abandoned.

[51] Int. Cl.$^2$ .............................................. C07C 85/04
[52] U.S. Cl. ................................................... 260/581
[58] Field of Search ............................ 260/581, 585 A

[56] References Cited

U.S. PATENT DOCUMENTS

| | | | |
|---|---|---|---|
| 1,840,760 | 1/1932 | Williams | 260/581 |
| 2,455,932 | 12/1948 | Hughes | 260/577 |
| 3,728,393 | 4/1973 | Gaige et al. | 260/585 A |
| 3,882,181 | 5/1975 | Forster et al. | 260/583 N |

FOREIGN PATENT DOCUMENTS

| | | | |
|---|---|---|---|
| 1,475,631 | 4/1967 | France | 260/501 |

OTHER PUBLICATIONS

Kanto, "Derwent Japanese Patent Abstracts", vol. 6, No. 4, pp. 5:6 (1967).
Parker, "Quarterly Reviews", vol. XVI, No. 2, pp. 163–187, (1962).
Shein et al., "Chem Ab", vol. 64, Ab. No. 19347b (1966).

*Primary Examiner*—Daniel E. Wyman
*Assistant Examiner*—John J. Doll
*Attorney, Agent, or Firm*—Anthony P. Mentis

[57] ABSTRACT p-Aminobenzotrifluoride is prepared by aminating p-chlorobenzotrifluoride in an essentially nonaqueous solvent in the presence of a catalyst system comprising a copper compound and a selected salt compound. Exemplary is the reaction of p-chlorobenzotrifluoride with ammonia in the presence of cuprous chloride and potassium fluoride to yield p-aminobenzotrifluoride.

23 Claims, No Drawings

PREPARATION OF P-AMINOBENZOTRIFLUORIDE

RELATED APPLICATION

This application is a continuation-in-part of application Ser. No. 647,495 filed Jan. 8, 1976 now abandoned.

BACKGROUND OF THE INVENTION

1. Field of the Invention p-Chlorobenzotrifluoride is aminaed in an essentially nonaqueous solvent in the presence of a catalyst system comprising certain copper compounds and salt compounds to produce p-aminobenzotrifluoride.

2. Prior Art

Aryl halides have been ammonolyzed in the presence of a copper compound such as cupric sulfate, Calcott, U.S. Pat. No. 2,062,349. They have also been ammonlyzed in the presence of a copper compound and an additional ingredient, as for example, lead dioxide (U.S. Pat. No 2,104,983); an oxide or hydrate of calcium, tin, lead, arsenic, or antimony (U.S. Pat. No. 2,391,848); saturated aqueous solution of sodium chloride (U.S. Pat. No. 2,455,932); an alkaline hydroxide alone or with an alkaline earth metal chloride (U.S. Pat. No. 1,840,760); a base comprising an alkaline earth metal oxide or hydroxide, an alkali metal hydroxide, or alkaline carbonate (British Pat. No. 370,774); an inorganic oxidant such as potassium chlorate alone or with a nitrate such as ammonium nitrate (U.S. Pat. No. 1,994,845); or ammonium chloride (Kanto, Derwent Japanese Patents Report 6, No. 4, p 5:6, 1967).

U.S. Pat. No. 3,484,487 patent to James S. Dix discloses the use of copper chloride and nonpolar organic solvents such as N-methylpyrrolidone, dimethylacetamide and hexamethylphosphoramide for amination of aryl halides. These solvents are not suitable for preparation of para-aminobenzotrifluoride since transamination occurs to a significant extent to form unwanted N-methylaminobenzotrifluoride and N,N-dimethylaminobenzotrifluoride.

T. Cohen and J. G. Tirpak, Tetrahedron Letters, 1975, 143 discuss Ullman couplings and ammonolyses of activated aryl halides catalyzed by copper compounds. No alkali metal or ammonium halide is used in their system and also aryl iodides and bromides are used which are known to aminate more readily than aryl chlorides.

Japanese 9110-637 to Mitsubishi filed Mar. 6, 1973, patented Oct. 22, 1974, abstracted in Derwent 16697W-10 (week of Mar. 11, 1975) is a process for preparing fluorobenzenes containing electron withdrawing groups in the ortho or para positions from chloro- or bromobenzenes by reaction with potassium fluoride catalyzed by cesium halides.

British Pat. No. 1,164,223 to Farbenfabriken Bayer A.-G. published Sept. 17, 1969, describes the preparation of trifluoromethylanilines by hydrolysis of the corresponding trifluoromethylphenyl isocyanates.

Daudt et al., U.S. Pat. Nos. 2,194,925 and 2,194,926 show the reaction of certain nitro-halo-benzotrifluorides with ammonia in a solvent medium and in the presence of a copper salt to produce nitro-amino-benzotrifluorides.

Zellner, Austrian Pat. No. 274,785, abstracted in Chemical Abstracts 71, page 400 (1969) prepared trifluoromethylanilines by reducing their corresponding N-acyl compounds with metal hydrides.

None of the prior art discloses the specific starting material reacted with ammonia in the presence of the unique catalyst combination shown herein.

DESCRIPTION OF THE INVENTION

It has been found that in the amination of of p-chlorobenzotrifluoride to produce p-aminobenzotrifluoride, the product p-aminobenzotrifluoride is readily hydrolyzed to p-aminobenzoic acid or aniline when aqueous amination processes of the prior art are used. Amination of p-chlorobenzotrifluoride in a nonaqueous medium using a copper compound as the sole catalyst significantly lessens the hydrolysis problem but produces only small amounts of the desired p-aminobenzotrifluoride. It has now been found that the use of a catalyst combination comprising a selected copper compound and a selected salt in a nonaqueous medium produces the desired product in good yields. It has been further found that the process also proceeds in the presence of a relatively small amount of water. This is advantageous where, as in continuous processes, it is desired to recycle the unreacted starting material and solvent containing relatively small amounts of water.

The invention is the process of reacting p-chlorobenzotrifluoride with ammonia in an essentially nonaqueous solvent which is nonreactive with p-aminobenzotrifluoride in the presence of a catalytically effective amount of a catalyst system comprising a selected copper compound and a selected salt at a superatmospheric pressure, at a temperature range of about 150°–240° C for a period of about 1 to 10 hours to produce p-aminobenzotrifluoride.

Suitable essentially nonaqueous solvents include those which are free of methylated nitrogen. They include p-chlorobenzotrifluoride itself, an alkanol of 1 to 5 carbon atoms, an aromatic nitrile containing 6 to 10 carbon atoms, an aliphatic dinitrile containing 4 to 6 carbons atoms and a glycol ether of the formula $R(OCH_2CH_2)_nOR^1$ wherein R is hydrogen or alkyl of 1–4 carbons, $R^1$ is alkyl of 1–4 carbons and $n=1$ to 3, and the like. Exemplary of suitable media are methanol, ethanol, 1-propanol, 2-propanol, 1-butanol, 2-butanol, 2-methyl-2-propanol, 2-methyl-1-propanol, 1-pentanol, 3-methyl-1-butanol, benzonitrile, acetonitrile, adiponitrile, diethylene glycol mono methyl ether, diethylene glycol mono ethyl ether, and diethylene glycol diethyl ether, etc.

Solvents which contain methylated nitrogen, e.g., hexamethylphosphoramide, dimethylformamide, etc., are disadvantageous since transamination occurs to give para-N-methylaminobenzotrifluoride and para-N,N-dimethylaminobenzotrifluoride as unwanted products.

When p-chlorobenzotrifluoride itself is used as the essentially nonaqueous medium, generally in excess of that needed to engage in the reaction, no additional discrete solvent is needed.

Preferred solvents are the alkanols and glycol ethers. More preferred are methanol, ethanol, and p-chlorobenzotrifluoride, and the preferred temperature range is 150°–240° C.

"Essentially nonaqueous solvent" means the reaction is carried out in the presence of up to about 10 weight % of water based on the weight of total liquids used, i.e., p-chlorobenzotrifluoride alone or p-chlorobenzotrifluoride and added solvent. It is preferred to use less than about 5 weight % of water, as in a continuous reaction.

Total pressure of the reactants varying from 30 to 400 atmospheres are useful. An excess of ammonia is generally used to generate the total pressure.

The catalyst system or combination can comprise one or more of the copper compound and one or more salt. The proportions of the components of the catalyst combination can vary over wide limits but it is generally best to have the salt in excess of the copper compound, as for example, molar ratios of 3:1 to 50:1.

The catalyst combinations should be present in catalytically effective amounts, i.e. amounts which significantly increase the production of the p-aminobenzotrifluoride; for example, for each mmol of p-chlorobenzotrifluoride there can be used 1 to 5 mmol of the designated salt and 0.05 to 0.60 mmol of copper compound.

Suitable copper compounds include cuprous chloride, cuprous bromide, cupric chloride, cupric bromide, copper sulfate, copper acetate, either hydrated or anhydrous, and the like.

Salts which are suitable include sodium fluoride, potassium fluoride, lithium fluoride, potassium chloride, lithium chloride, sodium bromide, potassium bromide, lithium bromide, sodium iodide, potassium iodide, lithium iodide, potassium acetate, magnesium fluoride, calcium fluoride, ammonium fluoride, ammonium chloride, ammonium bromide and ammonium iodide.

Salts which are preferred because of the good conversion and selectivity to p-aminobenzotrifluoride are

EXAMPLE 1

Four heavy-walled glass tubes, each having an internal volume of about 5 ml, were charged with the stated ingredients in runs, A, B, C and D below. All the reactants except the anhydrous ammonia gas were weighed into the tubes. The ammonia was condensed into the evacuated tubes, which were chilled in liquid nitrogen, from a calibrated flask using standard vacuum line techniques. Each tube was then sealed and all four were placed in a 400 ml shaker tube with 100 ml of ethanol as heat transfer fluid. An external pressure of 1400 psi of nitrogen was applied to the glass tubes in the shaker tube at −80° to prevent the tubes from breaking under the internal pressure generated at the reaction temperature. The shaker tube was then heated to 200° and maintained at this temperature for 10 hours. After cooling, the glass tubes were removed from the shaker tube, opened, and the excess ammonia allowed to distill off. The tube contents were then analyzed by either high pressure liquid chromatography (HPLC) or gas chromatography (GC). The results are given in Table 1 where runs A and B are representative of the prior art. The percentage conversion to product, which is the last column of the table, is based on the moles of starting material and the moles of product and is readily calculated by multiplying the figures in the preceding two columns and dividing the result by 100.

TABLE I

| Run | p-chlorobenzotrifluoride (g) | Solvent | Copper Compound (g) | Non-Copper Compound (g) | Ammonia Gas (g) | | % Conversion of p-chlorobenzotrifluoride (3) | % Yield of p-aminobenzotrifluoride (4) | % Conversion to p-amino benzotrifluoride (5) |
|---|---|---|---|---|---|---|---|---|---|
| A | 0.3316 | Ethanol | CuCl 1.2628 .0271 | — | 0.7858 | (HPLC) | 21.9 | 49.7 | 10.9 |
| B | 0.3241 | Ethanol | CuCl (1)1.2604 .0203 | — | 0.7719 | (GC) | 14.3 | 68.9 | 9.85 |
| C | 0.3351 | Ethanol | CuCl 1.2600 .0257 | KF 0.2444 | 0.7688 | (HPLC) | 54.4 | 74.4 | 40.5 |
| D | 0.3293 | Ethanol | CuCl (2)1.2577 .0223 | KF 0.2352 | 0.7625 | (GC) | 37.6 | 90.7 | 34.1 |

(1)Included 0.0141 g n-undecane as internal standard for G.C. analysis
(2)Included 0.01407 g n-undecane as internal standard for G.C. analysis.
(3)Percentage conversion is moles of unrecovered para-chlorobenzotrifluoride (usually equal to total moles of products)/moles of para-chlorobenzotrifluoride initially times 100.
(4)Percentage yield of para-aminobenzotrifluoride is moles of para-aminobenzotrifluoride produced/total moles of product times 100.
(5)Percentage conversion to para-aminobenzotrifluoride is percentage conversion times percentage yield divided by 100.

potassium fluoride, potassium chloride, potassium bromide, potassium iodide, calcium fluoride, magnesium flouride, ammonium fluoride and potassium acetate. Of this group potassium fluoride is most preferred.

In a preferred embodiment the reaction is carried out in methanol, ethanol, or excess of p-chlorobenzotrifluoride, using cuprous chloride and potassium fluoride.

The p-aminobenzotrifluoride can be recovered from the reaction by any conventional means as, for example, chromatography, distillation, solvent extraction, isolation as HCl salt, etc. For example, to isolate the HCl salt of the desired product, the final reaction mixture is diluted with solvent in which the HCl salt is insoluble, anhydrous HCl bubbled through the reaction mixture to form a precipitate of the HCl salt of p-aminobenzotrifluoride, and then filtered.

SPECIFIC EMBODIMENTS OF THE INVENTION

In the following illustrative examples all parts are by weight and all temperatures are Centigrade unless otherwise specified.

The data indicate the pressure of the KF catalyst component enhances by almost 4 times the percent conversion to p-aminobenzotrifluoride. The analyses were done according to one of the following procedures.

Cl High Pressure Liquid Chromatography

The procedure for this analysis consists of diluting the contents of the glass tubes to a total volume of 25 ml with a "carrier" solution composed of 79.7% cyclopentane, 20% chloroform, and 0.3% morpholine. From the 25 ml dilution, 1.0 ml (or sometimes 2.0 ml) is removed and further diluted to 100 ml with the carrier solution. A 100 microliter sample of the solution is injected into a 25 cm × 4.6 mm column of porous silicone microspheres −50 (6 μ partical size, 50Å pore size, 300m$^2$/g surface area, J. J. Kirkland NB E4294-149-3. See J. J. Kirkland, J. Chromatography, 83, 149 (1973)) at ambient temperature. A carrier solution flow rate of 2.86 ml/min at a pressure of 1000 psig is maintained, and the components as they elute are detected by ultraviolet absorption at a wavelength of 254 mm.

The percentage conversion and yield by this method of analysis are on a mole basis.

Gas Chromatography Analysis

The column was 8 foot × ⅛ inch Tenax GC 60/80. The column was maintained at 175° for 2 minutes after the sample was injected, then heated to 300° at 16°/min. The carrier gas flow rate was 50 cc/min.

An internal standard (n-undecane) was used in these analyses and percentage conversions and yields are also on a mole basis.

EXAMPLES 2-18

Following the general procedure of Example 1, additional experiments were carried out with the results shown in Table II. The data again show that when the non-copper component of the catalyst combination is omitted, the conversion of the starting material to p-aminobenzotrifluoride is low.

TABLE II

| Example | | p-chloro-benzotri-fluoride (g) | Solvent (g) | CATALYST Copper Compound (g) | | CATALYST Non-Copper Compound (g) | | $NH_3$ (g) | Temp. °C. | Time hours | % Conversion of p-chloro-benzotrifluoride | % Yield of p-amino benzotrifluoride |
|---|---|---|---|---|---|---|---|---|---|---|---|---|
| 2. | A | 0.3307 | Ethanol 1.2552 | CuCl | 0.0245 | KI | 0.7290 | 0.7127 | 200 | 5 | 21.7 | 37.8 |
|  | B | 0.3300 | Ethanol 1.2547 | CuCl | 0.0184 | KBr | 0.5315 | 0.7021 | 200 | 5 | 26.4 | 29.2 |
| 3. | A | 0.3279 | Ethanol 1.2623 | CuCl | 0.0225 | KF | 0.2608 | 0.6956 | 200 | 10 | 26.7 | 80.6 |
|  | B | 0.3366 | Ethanol 1.2575 | CuCl CuCl₂ | 0.0146 0.0059 | KF | 0.2472 | 0.7033 | 200 | 10 | 26.6 | 82.3 |
|  | C | 0.3299 | Ethanol 1.2561 | CuCl CuCl₂ | 0.0058 0.0142 | KF | 0.2615 | 0.7022 | 200 | 10 | 23.4 | 83.6 |
| 4. | A | 0.3308 | Ethanol 1.2760 | CuCl | 0.0213 | NaF | 0.1800 | 0.6862 | 200 | 10 | 11.2 | 56.6 |
|  | B | 0.3281 | Ethanol⁽¹⁾ 1.2649 | CuCl | 0.0201 | NaF | 0.1833 | 0.6712 | 200 | 10 | 10.1 | 56.3 |
|  | C | 0.3250 | Ethanol 1.2555 | CuCl | 0.0194 | KF | 0.2599 | 0.6438 | 200 | 10 | 13.8 | 90.7 |
|  | D | 0.3275 | Ethanol 0.6246 | CuCl | 0.0241 | KF | 0.2704 | 0.6508 | 200 | 10 | 5.9 | 97.2 |
| 5. | A | 0.3397 | Methanol 1.3103 | CuCl | 0.0214 | — | | 0.8838 | 200 | 5 | 10.1 | 74.7 |
|  | B | 0.3384 | Methanol 1.3070 | CuCl | 0.0210 | KF | 0.1255 | 0.8786 | 200 | 5 | 32.8 | 79.7 |
|  | C | 0.3396 | Methanol 1.3100 | CuCl | 0.0205 | KF | 0.2850 | 0.8867 | 200 | 5 | 30.2 | 76.4 |
|  | D | 0.3429 | Methanol 1.3109 | CuCl | 0.0215 | KF | 0.5402 | 0.8999 | 200 | 5 | 29.0 | 67.1 |
| 6 | | 0.3061 | Benzonitrile 1.4815 | CuCl | 0.0303 | KF | 0.1113 | 0.8101 | 190 | 2 | 23.2 | 98.5 |
| 7 | | 0.3190 | Methanol 1.2678 | CuSO₄ | 0.0528 | KF | 0.2116 | 0.8581 | 200 | 5 | 14.0 | 84.9 |
| 8 | | 0.3178 | Methanol 1.2695 | CuCl | 0.0325 | KCl | 0.2793 | 0.8564 | 200 | 5 | 16.6 | 64.6 |
| 9 | | 0.3315 | Ethanol 1.2967 | CuCl | 0.0197 | KO₂CCH₃ | 0.3294 | 0.7801 | 200 | 5 | 39.2 | 44.1 |
| 10 | | 0.3292 | Ethanol⁽¹⁾ 1.3006 | CuCl OCH₃ | 0.0203 | NH₄Br | 0.4210 | 0.7793 | 200 | 5 | 9.5 | 51.1⁽²⁾ |
| 11 | | 0.3500 | HO(CH₂)₂ 1.687 Diethylene glycol mono ethyl ether | CuCl | 0.0206 | KF | 0.2833 | 0.9039 | 200 | 5 | 23.3 | 88.9 |
| 12 | | 0.3028 | Pentanol 1.4646 | CuCl | 0.0304 | KF | 0.1005 | 0.8084 | 190 | 2 | 15.6 | 92.0 |
| 13 | | 0.3089 | 3-Methyl Butanol 1.2139 | CuCl | 0.0295 | KF | 0.0922 | 0.8102 | 190 | 2 | 13.5 | 82.2 |
| 14 | | 0.3037 | Propanol 1.2882 | CuCl | 0.0305 | KF | 0.1019 | 0.8032 | 190 | 2 | 9.9 | 82.7 |
| 15 | | 0.3499 | Ethanol 1.3665 | CuCl | 0.0229 | KF | 0.2764 | 0.9041 | 200 | 5 | 14.9 | 88.6 |
| 16 | | 0.3274 | Ethanol⁽¹⁾ 1.2547 | CuCl | 0.0222 | LiF | 0.1329 | 0.7025 | 200 | 10 | 14.8 | 58.7 |
| 17 | | 0.3496 | Ethanol 1.3493 | CuCl | 0.0216 | NH₄F | 0.1801 | 0.9217 | 200 | 5 | 10.3 | 85.5 |
| 18 | | 0.2820 | Ethanol 1.0743 | CuCl | 0.0166 | NH₄Cl KF | 0.0403 0.2217 | 0.7287 | 200 | 5 | 25.7 | 88.8 |

⁽¹⁾Also contained n-undecane as internal standard for G.C. Analysis - 0.01 g
⁽²⁾Includes p-bromobenzotrifluoride

EXAMPLES 19-22

Following the general procedure of Example 1, the following experiments were run in which the reaction was carried out at 200° C for 5 hours. Analysis of the products was done by high pressure liquid chromatography.

| Example | p-chloro benzotri-fluoride (g) | Solvent (g) | Water (g) | KF (g) | CuCl (g) | NH₃ (g) | % Conversion of p-chloro-benzotri-fluoride | % Yield of p-amino benzo-trifluoride |
|---|---|---|---|---|---|---|---|---|
| 19[1] | 0.3235 | Ethanol 1.2737 | 0.2044 | 0.1853 | 0.0292 | 0.8544 | 18.2 | 74.0 |
| 20[2] | 0.3249 | Ethanol 1.2067 | 0.0807 | 0.2064 | 0.0329 | 0.8667 | 20.0 | 84.8 |
| 21 | 0.3353 | Adiponitrile 1.3164 | — | 0.2044 | 0.0295 | 0.8987 | 45.3 | 73.7 |
| 22 | 2.6151 | — | — | 0.1927 | 0.0305 | 0.8660 | 3.54[3] | 99.2 |

[1]Weight % water is 11.3
[2]Weight % water is 5.0
[3]The % conversion in this example is based on the large excess of starting material, much of which is used as solvent.

EXAMPLES 23–31

A series of reactions which produced p-aminobenzotrifluoride were carried out in 5 ml sealed glass tubes containing in each instance 1.7 mmol of p-chlorobenzotrifluoride, 1.2 ml solvent, 3 to 4 mmol of non-copper compound, about 0.3 mmol of cuprous chloride and about 50 mmol of ammonia. The results are tabulated in the table below.

| Ex. | Non-Copper Compound | Solvent | Conditions °C | Hours | % Conversion | % Yield |
|---|---|---|---|---|---|---|
| 23 | LiCl | Methanol | 200 | 5 | 6.2 | 14.1 |
| 24 | NaBr | " | " | " | 13.3 | 18.6 |
| 25 | LiBr | " | " | " | 3.9 | 47.8 |
| 26 | NaI | " | " | " | 5.7 | 56.2 |
| 27 | LiI | " | " | " | 8.0 | 76.1 |
| 28 | NH₄Cl | " | " | " | 8.3 | 20.6 |
| 29 | NH₄I | " | " | " | 4.7 | 43.7 |
| 30 | MgF₂ | " | " | " | 18.0 | 53.0 |
| 31 | CaF₂ | " | " | " | 17.8 | 56.9 |

EXAMPLE 32

A mixture of 4.806 g of para-chlorobenzotrifluoride, 0.4991 g of cuprous chloride, 3.103 g of potassium fluoride, 13 g of ammonia, 17.9241 g of methanol, and 0.1961 g of n-undecane was heated at 200° C for 5 hrs in an 80 ml Hastelloy shaker tube. After cooling and venting the ammonia, the product mixture was removed. Most of the methanol and para-chlorobenzotrifluoride were distilled out of the product mixture. The remaining solution was diluted with diethyl ether and extracted with 0.5 M KOH to remove copper and ammonium salts as well as potassium fluoride. The ether layer was dried over CaSO₄. Vacuum distillation of the ether layer gave 0.55 g of para-aminobenzotrifluoride.

Para-aminobenzotrifluoride is a known compound and is a useful precursor for many para-substituted benzotrifluoride aromatic compounds. By conversion to its diazonium salt, followed by the well known diazonium transformations, para-aminobenzotrifluoride can be converted to para-hydroxy, fluoro, bromo, iodo, and cyanobenzotrifluoride. Furthermore, the diazonium salt can couple with itself or react with other compounds to form many compounds which are useful as dyes, insecticides, and herbicides.

I claim:

1. The process of reacting p-chlorobenzotrifluoride with ammonia in an essentially nonaqueous solvent in the presence of a catalytically effective amount of a catalyst combination comprising one or more compounds selected from the group consisting of cuprous chloride, cuprous bromide, cupric chloride, cupric bromide, copper sulfate and copper acetate and one or more additional compounds selected from the group consisting of potassium fluoride, potassium chloride, potassium bromide, potassium iodide, calcium fluoride, magnesium fluoride, ammonium fluoride and potassium acetate at a pressure in the range of 30 to 400 atmospheres, at a temperature range of about 150°–240° C for a period of about 1 to 10 hours to produce p-aminobenzotrifluoride.

2. The process of claim 1 in which the essentially nonaqueous solvent is p-chlorobenzotrifluoride, an alkanol of 1–5 carbons, an aromatic nitrile of 6 to 10 carbons, an aliphatic dinitrile of 4 to 6 carbons or a glycol ether of the formula $R(OCH_2CH_2)_nOR^1$ in which R is hydrogen or alkyl of 1–4 carbons, $R^1$ is alkyl of 1–4 carbons and $n=1$ to 3.

3. The process of claim 1 in which water is present up to about 10 weight % based on the weight of the starting p-chlorobenzotrifluoride alone or with added solvent.

4. The process of claim 1 in which the solvent is an excess of p-chlorobenzotrifluoride.

5. The process of claim 1 in which the solvent is an aromatic nitrile.

6. The process of claim 1 in which the solvent is an aliphatic dinitrile.

7. The process of claim 1 in which the solvent is an alkanol.

8. The process of claim 1 in which the solvent is methanol.

9. The process of claim 1 in which the solvent is ethanol.

10. The process of claim 1 in which the solvent is diethyleneglycol monoethyl ether.

11. The process of claim 1 in which the copper compound is cuprous chloride.

12. The process of claim 1 in which the copper compound is cupric chloride.

13. The process of claim 1 in which the copper compound is a mixture of cuprous chloride and cupric chloride.

14. The process of claim 1 in which the additional compound is potassium fluoride.

15. The process of claim 1 in which the additional compound is potassium chloride.

16. The process of claim 1 in which the additional compound is potassium iodide.

17. The process of claim 1 in which the additional compound is potassium bromide.

18. The process of claim 1 in which the additional compound is calcium fluoride.

19. The process of claim 1 in which the additional compound is magnesium fluoride.

20. The process of claim 1 in which the additional compound is ammonium fluoride.

21. The process of claim 1 in which the additional compound is potassium acetate.

22. The process of claim 1 in which the solvent is ethanol and the catalyst combination comprises cuprous chloride and potassium fluoride.

23. The process of claim 1 in which the solvent is an excess of p-chlorobenzotrifluoride and the catalyst combination comprises cuprous chloride and potassium fluoride.

* * * * *